United States Patent [19]

Edge

[11] Patent Number: 5,746,218
[45] Date of Patent: May 5, 1998

[54] THERAPEUTIC PILLOW

[76] Inventor: David A. Edge, 5447 Rowe Trail, Pace, Fla. 32571

[21] Appl. No.: 691,344

[22] Filed: Aug. 2, 1996

[51] Int. Cl.$^6$ .................................................. A61G 15/00
[52] U.S. Cl. ........................... 128/845; 128/DIG. 20; 128/882; 5/648
[58] Field of Search .................................. 128/845, 846, 128/882, DIG. 20; 602/13, 19; 5/630, 648, 649, 650, 636

[56] References Cited

U.S. PATENT DOCUMENTS

| | | | |
|---|---|---|---|
| 1,845,338 | 2/1932 | Querna | 128/882 |
| 3,345,656 | 10/1967 | Steinman | 5/650 |
| 3,604,023 | 9/1971 | Lynch | 5/650 |
| 4,390,015 | 6/1983 | Clements | 128/80 |
| 4,805,605 | 2/1989 | Glassman | 128/882 |
| 4,905,678 | 3/1990 | Cumins | 602/19 |
| 5,117,522 | 6/1992 | Everett | 5/648 |
| 5,125,123 | 6/1992 | Engle | 5/648 |
| 5,216,771 | 6/1993 | Hoff | 5/648 |
| 5,279,310 | 1/1994 | Hsien | 128/845 |
| 5,377,693 | 1/1995 | Loper et al. | 128/845 |
| 5,476,105 | 12/1995 | Toth | 128/845 |

*Primary Examiner*—Michael A. Brown
*Attorney, Agent, or Firm*—Peter Loffler

[57] ABSTRACT

A therapeutic pillow for holding a person's legs together during sleep includes a generally upwardly sloping and then generally downwardly sloping base. A first thigh receiving region extends upwardly from the base while a second thigh receiving region extends upwardly from the base in mirror-image symmetrical fashion to the first thigh receiving region. A first calf receiving region extends upwardly from the base while a second calf receiving region extends upwardly from the base in mirror-image symmetrical fashion to the first calf receiving region.

11 Claims, 2 Drawing Sheets

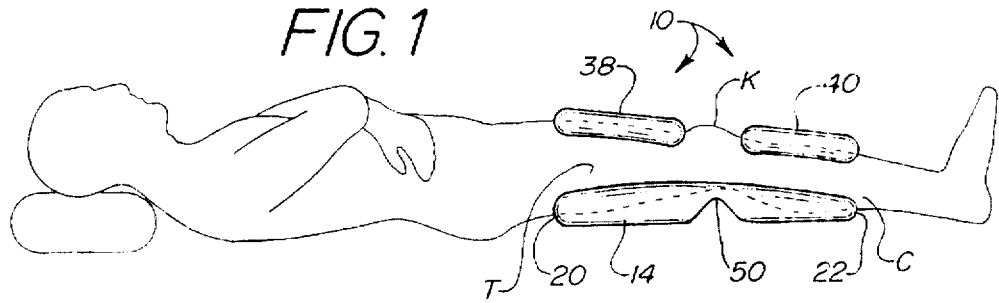
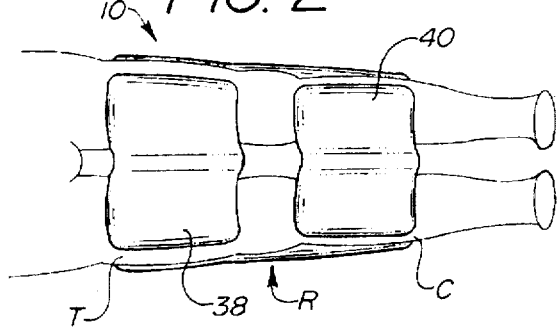
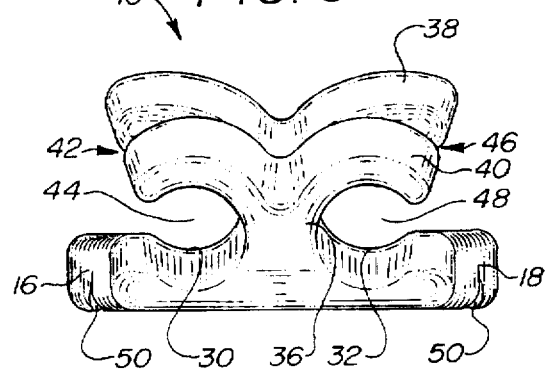
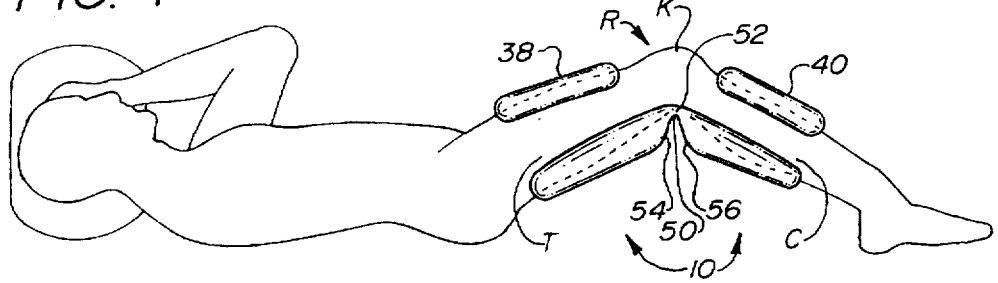
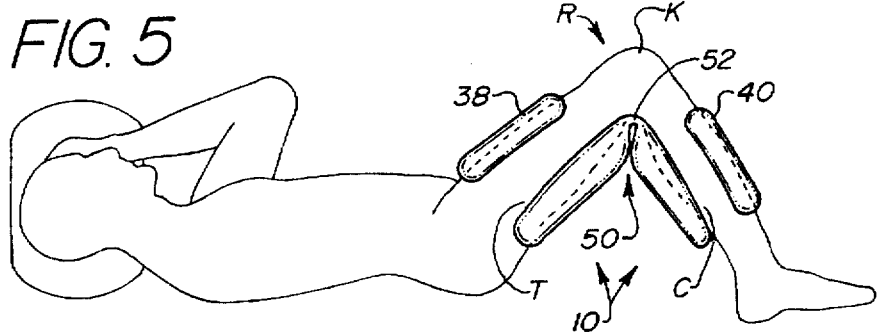

THERAPEUTIC PILLOW

BACKGROUND OF THE INVENTION

1. Field of the Invention

The present invention relates to a therapeutic pillow for keeping a user's legs together during sleep.

2. Background of the Prior Art

Most people will suffer an episode of debilitating back pain at some point in their lives, with the majority of the pain emanating from the lower back. The back pain can be aggravated during sleep. When a person is lying on his back, stress is placed on the coccyx and sacroiliac joints resulting in sciatic nerve strain. In order to overcome this stress, a person lies on his side. However, this results in the upper leg crossing over and resting beyond the lower leg causing pelvic twisting which causes rotation of the last two vertebrae which in turn results in torsional strain in spinal soft tissue.

In order to overcome such problems during sleep, doctors recommend that a person sleep on his side with a pillow between his legs. The pillow keeps the two legs together denying pelvic rotation and thus eliminating back strain. Furthermore, the pillow keeps the medial portion of the knees nocturnally separated, eliminating buildup of the cutaneous and subcutaneous pressure ischemia. By way of example, U.S. Pat. No. 5,216,771 to Hoff was specifically designed for such a nocturnal therapeutic pillow. However, the problem with the Hoff invention, as well as regular pillows placed between a user's legs during sleep, is the inability of the pillow to remain therebetween throughout the night. As a user moves during the night, the pillow slips out from between the legs and its therapeutic value is lost for the remainder of the sleep cycle.

Other devices in the art suffer from the above and other problems.

Therefore, there is a need in the art for a therapeutic pillow that is nocturnally placeable between a user's legs, while the user lies on his side, and remains so positioned throughout the sleep cycle. The device must eliminate improper pelvic rotation by keeping the legs coextensive with each other. The device should keep the knees comfortably apart during device use. The device must be of simple and straightforward design and must be comfortable to use.

SUMMARY OF THE INVENTION

The therapeutic pillow of the present invention addresses the aforementioned needs in the art. The therapeutic pillow receives a user's thighs and calves and holds the user's legs together during sleep, while keeping the medial portion of the knees from contacting each other.

The therapeutic pillow is comprised of a base having a top portion, medial portion, and a bottom portion, and a top surface and a bottom surface. The top surface slopes upwardly from the top portion to the medial portion, then slopes downwardly to the bottom portion. A first generally concave thigh receiving region having an opening facing outwardly extends from the top portion to the medial portion while a second generally concave thigh receiving region having an opening facing outwardly in opposite direction to first thigh receiving region opening extends from the top portion to the medial portion in mirror-image symmetrical fashion to the first thigh receiving region. The distance between the two thigh receiving regions is greater proximate the top portion then proximate the medial portion. A first generally concave calf receiving region having an opening facing outwardly extends from the medial portion to the bottom portion while a second generally concave calf receiving region having an opening facing outwardly in opposite direction to first calf receiving region opening extends from the medial portion to the bottom portion in mirror-image symmetrical fashion to the first calf receiving region. The distance between the two calf receiving regions is generally equal throughout the extension of the calf receiving regions. An open region exists between the first thigh receiving region and the first calf receiving region as well as between the second thigh receiving region and the second calf receiving region. Optional straps can be used to hold the person's limbs within their respective regions.

A pair of generally coextensive troughs extend from the top portion to the bottom portion such that the first trough extends the concavity of the first thigh receiving region and the first calf receiving region while the second trough extends the concavity of the second thigh receiving region and the second calf receiving region A V-notch is located on the medial portion of the base, below the open region, to permit device flexure.

The device, being made from a soft, resilient material such as foam, air cushion, and the like comfortably receives a person's legs and holds them together while a person sleeps on his side. As a result, rotational stresses in the lower lumbar spine, brought on by pelvic twisting, are reduced. Impingement stresses in the coccyx and sacroiliac joints are reduced, creating anatomically neutral body position and thereby creating slack within the sciatic nerves reducing lower leg or lower extremity discomfort.

The device allows the lumbar spine to be placed in a flattened or hypolordotic position, thereby reducing stress on the lumbar intervertebral disc, facets, and supportive soft tissues. By reducing the risk of nocturnal axial rotation of the lumbar spine, the therapeutic pillow of the present invention palliates a great number of chronic spinal conditions, such as spondylosis, sciatica, disc protrusions and herniations, and a whole myriad of soft tissue conditions like strains, sprains, and slipped discs.

The device allows full arch of movement at the knee for nocturnal movement and stretching. Furthermore, as the device actively separates the medial portions of both knees, nocturnal contact or buildup of cutaneous or subcutaneous pressure ischemia is eliminated.

BRIEF DESCRIPTION OF THE DRAWINGS

FIG. 1 is a side view of the therapeutic pillow of the present invention in use.

FIG. 2 is a top view of the therapeutic pillow in use.

FIG. 3 is an end view of the therapeutic pillow.

FIGS. 4 and 5 illustrate the ability of device flexure with a user's legs contained therein while

Similar reference numerals refer to similar parts throughout the several views of the drawings.

DETAILED DESCRIPTION OF THE PREFERRED EMBODIMENT

Figure 6:
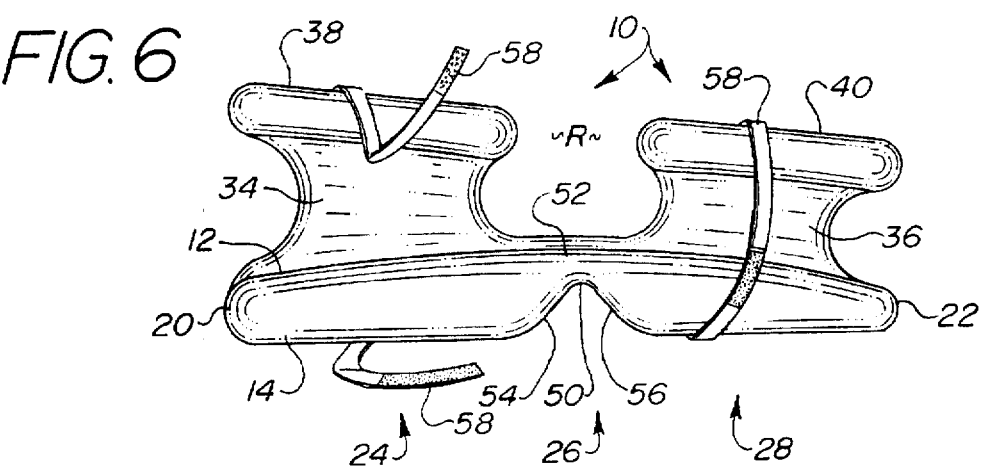
FIGS. 6–8 illustrate the range of device flexure without illustrating the user's legs.
Figure 7:
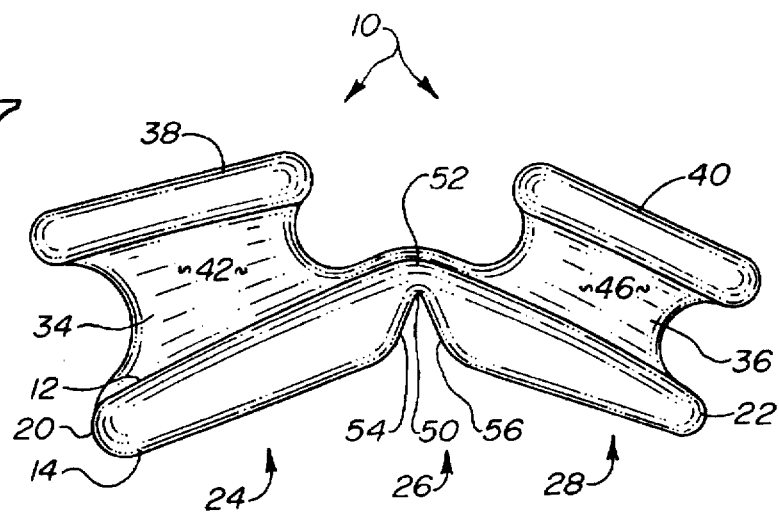
Figure 8:
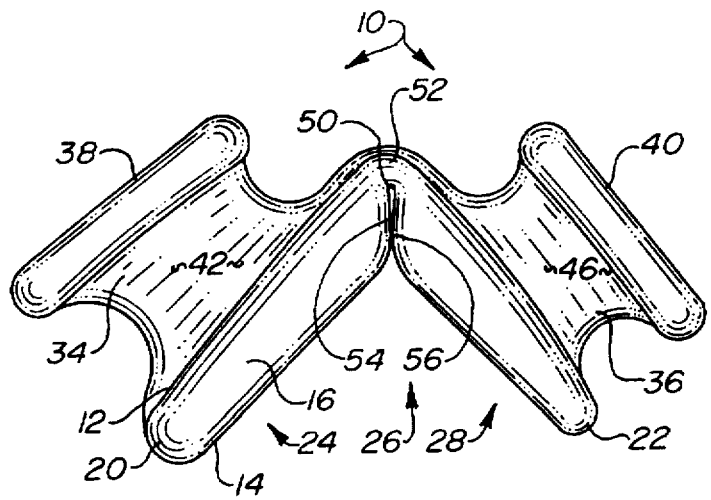

Referring now to the drawings, it is seen that the therapeutic pillow of the present invention, generally denoted by reference numeral 10, is comprised of a base having a top surface 12, a bottom surface 14 which is generally flat, a first side 16 which is generally flat, a second side 18 which is generally flat, a front 20, a rear 22, a top portion 24, a medial portion 26, and a bottom portion 28. A first trough 30 and a second trough 32 extend along the length of the base, from the top portion 24 to the bottom portion 28, disposed within the top surface 12. The first trough 30 slopes upwardly from the top portion 24 to the medial portion 26 and then slopes downwardly to the bottom portion 28. The second trough 32 slopes upwardly from the top portion 24 to the medial portion 26 and then slopes downwardly to the bottom portion 28. The first trough 30 and the second trough 32 are each generally concave. The distance between the first trough 30 and the second trough 32 is greater at the top portion 24 than at the medial portion 26 and the distance tapers from the top portion 24 to the medial portion 26 in generally linear fashion, while the distance between the first trough 30 and the second trough 32 is generally similar at the medial portion 26 and at the bottom portion 28.

A first separator 34 extends upwardly from the top surface 12 of the base's top portion 24, while a second separator 36 extends upwardly from the top surface 12 of the base's bottom portion 28. A first plate 38 extends outwardly in both directions from the top of the first separator 34, while a second plate 40 extends outwardly in both directions from the top of the second separator 36. As seen, the first separator 34 and the first plate 38 continue the concave nature of the first trough 30 and define a right thigh receiving region 42 while the first separator 34 and the first plate 38 continue the concave nature of the second trough 32 and define a left thigh receiving region 44. The second separator 36 and the second plate 40 continue the concave nature of the first trough 30 and define a right calf receiving region 46 while the second separator 36 and the second plate 40 continue the concave nature of the second trough 32 and define a left calf receiving region 48. An open region R exists between the right and left thigh receiving regions 42 and 44 and the right and left calf receiving regions 46 and 48.

As seen, the bottom surface 14, proximate the medial portion 26, beneath the open region R, has a V-shaped notch 50 extending upwardly toward the top surface 12 and defining a hinge 52 on the base, the notch 50 having a first face 54 and a second face 56.

All outer edges and corners of the device 10 are rounded for increased user comfort.

In order to use the leg pillow 10 of the present invention, a user places his right thigh T into the right thigh receiving region 42 and his right calf C into the right calf receiving region 44. The user places his left thigh (not illustrated) into the left thigh receiving region 46 and his left calf (not illustrated) into the left calf receiving region 48. The concave nature of the various thigh and calf receiving regions allows the device 10 to comfortably receive the legs of the user. The user's knees protrude through the open region R.

If desired, optional straps 58 can be used to hold the thighs and calves of the user within the device 10. The straps 58 have mating means of any appropriate design including Velcro, buckle, snaps, etc.

When the user is lying on his side, the device 10 receives the user's legs, holds them together and relieves pressure from the hips and the lower back. The sloping nature of the first trough 30 and the second trough 32 conform to the natural slope of the legs of the human body. The first separator 34 provides separation of the user's thighs. The tapered nature of the first separator 34 conforms to the human body's natural decreasing separation of the legs from the pelvis to the knees. The flat nature of the two sides 16 and 18 of the base provide stability to the device whenever the user lies on his side.

The notch 50 permits a user to flex his knees while using the device 10. As the user flexes his knees, the hinge 52 flexes and permits the top portion 24 to flex relative to the bottom portion 28. At the miter angle of the notch 50, the first face 54 abuts the second face 56 and prohibits further bending of the user's legs. As the top portion 24 slides upward along the user's thighs when the user bends his legs, the top portion 24 and the two thigh receiving regions 42 and 44 are dimensioned so as to not interfere or otherwise cause discomfort to the user's groin area during maximum leg bend.

Advantageously, the device 10 will be constructed from a relatively soft material, such as a closed-cell foam and the entire device 10 will be a single integral unit.

While the invention has been particularly shown and described with reference to an embodiment thereof, it will be appreciated by those skilled in the art that various changes in form and detail may be made without departing from the spirit and scope of the invention.

I claim:

1. A therapeutic pillow for receiving a user's thighs and calves and holding the user's legs together during sleep comprising:

a base, having a top portion, a medial portion, a bottom portion, a top surface, a bottom surface, a front, a rear, a left side, and a right side;

a first generally concave thigh receiving region, having a first opening facing outwardly, extending upwardly from the top surface and extending from the top portion to the medial portion, for receiving a user's right thigh;

a second generally concave thigh receiving region, having a second opening facing outwardly, extending upwardly from the top surface and extending from the top portion to the medial portion in mirror-image symmetrical fashion to the first thigh receiving region, for receiving a user's left thigh;

a first generally concave calf receiving region, having a third opening facing outwardly, extending upwardly from the top surface and extending from the medial portion to the bottom portion, for receiving a user's right calf;

a second generally concave calf receiving region, having a fourth opening facing outwardly, extending upwardly from the top surface and extending from the medial portion to the bottom portion in mirror-image symmetrical fashion to the first calf receiving region, for receiving a user's left calf; and such that an open region exists between the first thigh receiving region and the first calf receiving region as well as between the second thigh receiving region and the second calf receiving region.

2. The device as in claim 1 wherein the top surface slopes upwardly from the top portion to the medial portion and then slopes downwardly from the medial portion to the bottom portion.

3. The device as in claim 1 wherein the distance between the first thigh receiving region and the second thigh receiving region is greater proximate the top portion then proximate the medial portion.

4. The device as in claim 3 wherein the decrease in distance between the first thigh receiving region and the second thigh receiving region from the top portion to the medial portion decreases in generally linear fashion.

5. The device as in claim 1 further comprising:
a first set of one or more straps attached to the first thigh receiving region for holding the right thigh therein;
a second set of one or more straps attached to the second thigh receiving region for holding the left thigh therein;
a third set of one or more straps attached to the first calf receiving region for holding the right calf therein; and
a fourth set of one or more straps attached to the second calf receiving region for holding the left thigh therein.

6. The device as in claim 1 further comprising a V-notch within the bottom surface at the medial portion.

7. The device as in claim 1 further comprising:
a first trough extending from the top portion to the bottom portion, such that the first trough extends the concavity of the first thigh receiving region and the first calf receiving region; and
a second trough extending from the top portion to the bottom portion, such that the second trough extends the concavity of the second thigh receiving region and the second calf receiving region.

8. The device as in claim 7 wherein the distance between the first trough and the second trough is greater proximate the top region then proximate the medial region.

9. The device as in claim 1 wherein the device is constructed from closed cell foam.

10. The device as in claim 1 wherein all outer edges are rounded and all outer corners are rounded.

11. The device as in claim 1 wherein the left side is generally flat and the right side is generally flat.

* * * * *